United States Patent [19]
Dubats et al.

[11] Patent Number: 5,893,367
[45] Date of Patent: Apr. 13, 1999

[54] THERAPEUTIC GAIT HARNESS AND PELVIC SUPPORT SYSTEM

[76] Inventors: David Edward Dubats; Barbara Ann Dubats, both of 117 Neptune La., Holmes Beach, Fla. 34217

[21] Appl. No.: 09/048,759

[22] Filed: Mar. 26, 1998

Related U.S. Application Data

[60] Provisional application No. 60/041,719, Mar. 27, 1997.
[51] Int. Cl.$^6$ ............................................. A61F 5/37
[52] U.S. Cl. .......................... 128/875; 602/19; 128/882
[58] Field of Search ............................. 128/846, 869, 128/874, 875, 876, 882, 95.1, 96.1, 98.1, 100.1; 602/19; 297/485, 486

[56] References Cited

U.S. PATENT DOCUMENTS

| | | | |
|---|---|---|---|
| 1,047,457 | 12/1912 | Steimer | 128/882 |
| 3,776,540 | 12/1973 | Comando | 128/882 |
| 4,905,678 | 3/1990 | Cumins | 602/19 |
| 5,172,703 | 12/1992 | Tiede | 128/875 |
| 5,190,055 | 3/1993 | O'connor | 128/869 |
| 5,256,135 | 10/1993 | Avihod | 128/874 |
| 5,397,171 | 3/1995 | Leach | 128/825 |
| 5,564,788 | 10/1996 | Warhaftig | 128/869 |
| 5,690,122 | 11/1997 | Weber-Unger | 602/19 |

*Primary Examiner*—Michael A. Brown
*Attorney, Agent, or Firm*—Ronald E. Smith

[57] ABSTRACT

A therapeutic gait harness worn by a patient includes a padded thoracic harness that substantially encircles the patient's waist and which includes a plurality of circumferentially spaced hand holds and clamp-engageable rings that facilitate lifting, holding, manipulation and guidance of a patient who requires help in sitting, standing, or walking. An adjustable belt spans the gap between the opposing ends of the thoracic harness and is used to comfortably tighten the thoracic harness about the wearer's waist. A pelvic support harness depends from the thoracic harness and is detachably secured to the thoracic harness by an elongate zipper. A pair of flat leg straps depend from the pelvic support harness and terminate in thigh straps. Hook and loop fasteners are employed to comfortably secure the thigh straps to the wearer's thighs.

9 Claims, 2 Drawing Sheets

THERAPEUTIC GAIT HARNESS AND PELVIC SUPPORT SYSTEM

This application claim the benefit of U.S. Provisional Application No. 60/041,719 filed Mar. 27, 1997.

BACKGROUND OF THE INVENTION

1. Field of the Invention

This invention relates, generally, to mechanical prosthetic and therapeutic aids employed by physical and occupational therapists when administering standing and walking therapies to disabled, infirm, or geriatric patients. More particularly, it relates to an assistive device used by caregivers to lift, transport, and support individuals in their care.

2. Description of the Prior Art

There are a number of harnesses worn by patients that are of general assistance to care-givers. However, there are no known all-in-one harnesses that help a patient sit up from a reclining position, help a patient stand from a sitting position, help a patient walk, help a patient sit down from a standing position, and help a patient lie down from a sitting position. Moreover, there are no known harnesses that enable a care giver to hold the harness in such a way as to guide and stabilize the patient in a way that is comfortable to the patient and the care giver, nor are there any known harneses that can be releasably engaged by mechanical clamps or the like to further assist the care giver. Nor was it known heretofore how to provide a padded thoracic harness and an unpadded pelvic support harness including thigh straps all in one harness, and how to make the two harnesses separable from one another.

In view of the art considered as a whole at the time the present invention was made, it was not obvious to those of ordinary skill in this art how the needed therapeutic gait harness and pelvic support system could be provided.

SUMMARY OF THE INVENTION

The longstanding but heretofore unfulfilled need for an apparatus that overcomes the limitations of the prior art is now met by a new, useful, and nonobvious invention. The novel therapeutic gait harness and pelvic support system includes a padded thoracic harness in the form of a flexible material that is adapted to at least partially encircle a wearer's waist, a pelvic support harness that is connected to and that depends from the thoracic harness and which is adapted to at least partially encircle a wearer's waist, a pair of leg straps that are connected to and which depend from the pelvic support harness, and a thigh strap connected to a free end of each of the leg straps. Each thigh strap is adapted to adjustably encircle a patient's thighs.

A belt means is connected to the thoracic harness; it is adapted to adjustably secure the thoracic harness in tight but comfortable relation to said patient's waist.

A plurality of hand holds and a plurality of clamp-engageable rings are attached to the thoracic harness in circumferentially spaced relation to one another.

An elongate zipper having a circumferential extent substantially equal to the substantially common circumferential extent of the thoracic harness and the pelvic support harness detachably secures said harnesses to one another.

It is therefore understood that a primary object of this invention is to provide a safe device that helps patients maintain a correct, upright posture while learning to walk again after losing their ability to do so.

Another object is to provide a device that makes it easier for therapists and aides to hold, support, guide and manipulate patients as they are transferred from one location to another or as they sit up, stand up, or walk.

Yet another object is to provide a therapeutic gait harness that is comfortable to wear and which gives patients a sense of security.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
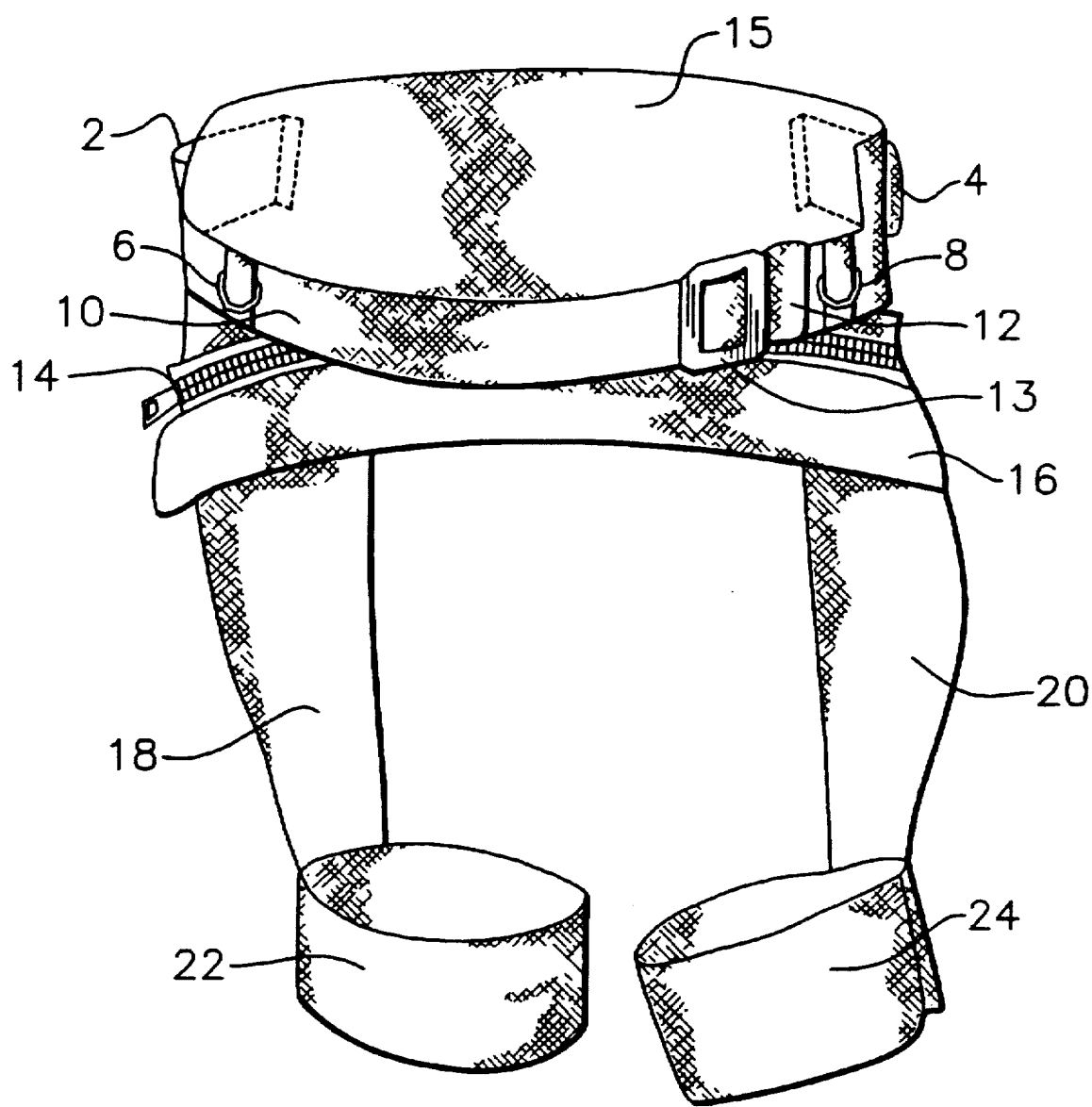
FIG. 1 is a front perspective view of a preferred embodiment of the invention.
Figure 2:
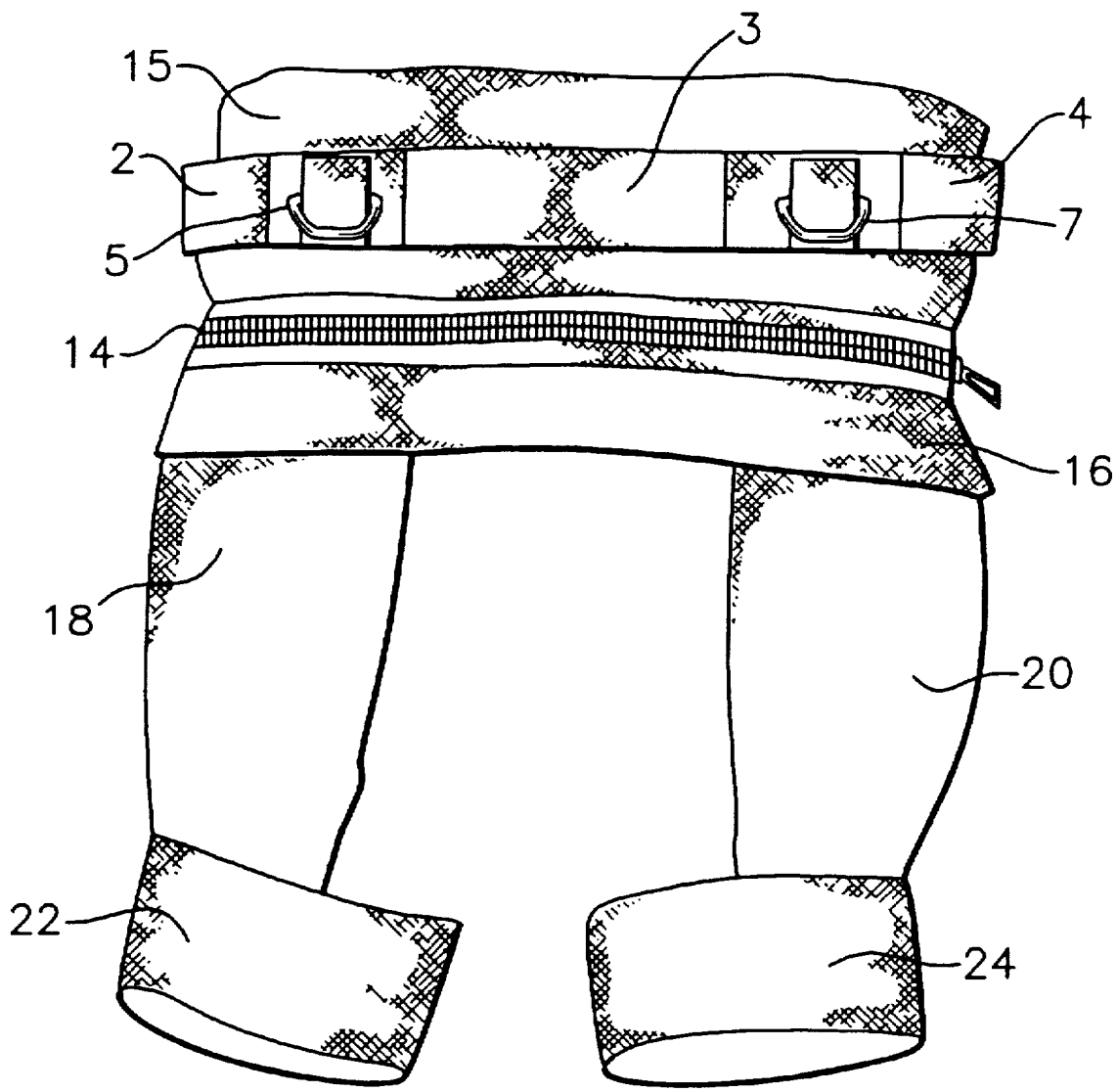
FIG. 2 is a rear perspective view thereof.

Referring now to FIGS. 1 and 2, it will there be seen that an exemplary embodiment of the invention is depicted in front and rear views, respectively.

The novel system includes a thoracic harness 15 which is formed of a flexible, padded material and an unpadded pelvic support harness 16.

A plurality of hand holds, denoted 2, 3 and 4, are sewn or otherwise permanently attached to thoracic harness 15 in circumferentially spaced relation to one another as depicted; each hand hold is formed by a strip of slip-resistant, nonconductive, and compressible material that is secured at its opposite ends to said thoracic harness 15. Note that the hand holds overlie the waist area of a patient wearing novel assembly 10, and that they are specifically positioned so that they may be grasped by a care-giver while maintaining a neutral wrist posture.

Thoracic harness 15 and pelvic support harness 16 share a common extent and substantially but not completely encircle a patient's waist. Belt means 10 adjustably bridges the gap between opposed ends of thoracic harness 15 when said harness 15 is worn. A first end of belt means 10 includes a loop 12, secured to a free end of thoracic harness 15, that captures a first end of buckle 13 that adjustably receives a second, free end of the belt means in the well-known way so that the novel system may be worn by people of varying girths.

It should be understood that FIG. 1 depicts belt means 10 when buckle 13 and the free end of the belt are coupled to one another, i.e., padded thoracic harness 15, like pelvic support harness 16, does not extend completely around a wearer's waist when the novel gait harness is worn.

Loop-shaped ring members 5, 6, 7 and 8 are secured by suitable means about the circumference of thoracic harness 15. Each ring member is of rigid construction and includes a base that is captured by a strip of material that is sewn or otherwise secured to thoracic harness 15. Rings 5, 6, 7 and 8 are clamp-engageable.

As a practical matter, hand holds 2, 3 and 4 are preferably formed by sewing a strip of fabric at preselected points to padded member 15; the unnumbered vertical lines closely flanking rings 5 and 7 in FIG. 2 represent such sewing lines.

Zipper means 14 interconnects padded thoracic harness 15 and unpadded pelvic support harness 16. More particularly, the upper part of the fabric part of zipper means 14 is sewn or otherwise secured to an unpadded lowermost edge of padded thoracic harness 15, and the lower part of the fabric part of said zipper means is similarly secured to the uppermost edge of pelvic support harness 16 as depicted.

Legs 18 and 20 are sewn or otherwise secured to and depend from unpadded pelvic support harness assembly 16; said legs are flat strips of material that overlie a patient's thighs when in use. Thigh straps 22, 24 are secured to the respective free ends of legs 18, 20 and each strap forms a loop that encircles a patient's thigh an inch or so above the knee. Suitable fastening means are secured to the opposite ends of each strap to releasably and adjustably secure said opposite ends of said thigh straps 22, 24 to one another in secure but comfortable encircling relation to a patient's thighs; hook and loop fastening members are one form of suitable fastening means.

When the novel gait harness is worn by a patient, upper thoracic harness assembly 15 substantially encircles the patient's waist, lower pelvic support harness assembly 16 is attached to assembly 15, and thigh straps 22, 24 cooperate with belt means 10 to secure the device to the patient.

The novel gait harness may be used to raise a patient from a reclining position to a sitting position and from a sitting position to a standing position. It may also be used to support and guide a patient from a standing position to a walking movement. Further, it has utility in helping a patient return to a seated position from a standing position, and so on. It is safe when used properly and provides many benefits to the patient while facilitating the work of the care giver.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A therapeutic gait harness and pelvic support system, comprising:

a thoracic harness in the form of a flexible material that is adapted to at least partially encircle a wearer's waist;

a pelvic support harness that is connected to and that depends from said thoracic harness and which is adapted to at least partially encircle a wearer's waist;

a pair of leg straps that are connected to and which depend from said pelvic support harness;

a thigh strap connected to a free end of each of said leg straps;

each thigh strap adapted to adjustably encircle a patient's thighs; and a belt means connected to said thoracic harness, said belt means adapted to adjustably secure said thoracic harness in tight but comfortable relation to said patient's waist.

2. The assembly of claim 1, further comprising a plurality of hand holds attached to said thoracic harness in circumferentially spaced relation to one another.

3. The assembly of claim 2, further comprising a plurality of clamp-engageable ring members attached to said thoracic harness in circumferentially spaced relation to one another.

4. The assembly of claim 1, further comprising attachment means for detachably securing said pelvic support harness to said thoracic harness.

5. The assembly of claim 4, wherein said thoracic harness and said pelvic support harness share a substantially common circumferential extent.

6. The assembly of claim 5, wherein said attachment means is an elongate zipper having a circumferential extent substantially equal to said substantially common circumferential extent of said thoracic harness and said pelvic support harness.

7. The assembly of claim 1, wherein said thoracic harness is padded to enhance the comfort of a wearer.

8. The assembly of claim 1, wherein said pelvic support harness, said leg straps, and said thigh straps are unpadded.

9. The assembly of claim 1, further comprising hook and loop fastener members secured to opposite ends of each of said thigh straps for adjustably connecting said thigh straps to said thighs.

* * * * *